United States Patent [19]

Hillman et al.

[11] Patent Number: 4,523,928

[45] Date of Patent: Jun. 18, 1985

[54] GASOHOL PRODUCTION FROM THERMOCHEMICAL CONVERSION OF BIOMASS TO ETHANOL

[75] Inventors: Melville E. D. Hillman, Columbus; William J. Huffman, Worthington; Edward S. Lipinsky, Columbus; Edgel Stambaugh, Worthington, all of Ohio

[73] Assignee: Battelle Development Corporation, Columbus, Ohio

[21] Appl. No.: 144,190

[22] Filed: Apr. 28, 1980

[51] Int. Cl.$^3$ .............................................. C10L 1/18
[52] U.S. Cl. ............................................. 44/56; 44/53; 44/68; 568/920; 568/921; 568/922
[58] Field of Search ............... 44/56, 68, 53; 568/876, 568/878, 913, 920, 921, 922

[56] References Cited

U.S. PATENT DOCUMENTS

| | | | |
|---|---|---|---|
| 1,496,810 | 6/1924 | Keyes | 44/56 |
| 1,527,504 | 2/1925 | Backhaus | 44/56 |
| 1,578,201 | 3/1926 | Midgley, Jr. | 44/56 |
| 2,177,557 | 10/1939 | Bergstrom et al. | 202/5 |
| 2,382,889 | 8/1945 | Lock | 562/515 |

OTHER PUBLICATIONS

Hanriot, "Sur la Decomposition Pyrogenee des Acides de la Serie Grasse", *Nouv. Ser.*, T. XLV, Societe Chimique, pp. 79–81, (1886).

Fischer Schrader and Wolter, "Uber die Entkarboxylierung der Milschaure", Gesamm. Abh. Kenntni Kohle, 6, 99–107, 1923.

*Primary Examiner*—Jacqueline V. Howard
*Attorney, Agent, or Firm*—Benjamin Mieliulis; Jerry K. Mueller, Jr.

[57] ABSTRACT

Disclosed is a method for thermochemically converting a carbohydrate material into ethanol wherein the carbohydrate material and a metal salt are reacted at elevated temperature to form an intermediate carbohydrate complex salt and/or a lactate metal salt which then is pyrolyzed in the presence of water into ethanol. Preferred carbohydrate materials for the process are various sugars and the metal salt preferably is a metal oxide, hydroxide, or carbonate. The intermediate complex and/or lactate salt may be separated from its aqueous reaction mixture prior to its pyrolysis to reduce the ultimate separation of ethanol from water. Alternatively, the metal of the metal salt may be one whose carbonate decomposes to metal oxide and carbon dioxide during the pyrolysis step of the process to generate said metal salt in situ.

24 Claims, No Drawings

GASOHOL PRODUCTION FROM THERMOCHEMICAL CONVERSION OF BIOMASS TO ETHANOL

CROSS-REFERENCE TO RELATED APPLICATIONS

This application is cross-referenced to commonly assigned application U.S. Ser. No. 144,189, of Hillman, entitled "One-Step Catalytic Thermochemical Conversion of Biomass of Ethanol", and to U.S. Ser. No. 144,194, of Hillman et al, entitled "Multi-Step Thermochemical Conversion of Biomass to Ethanol", both being filed on even date herewith.

BACKGROUND OF THE INVENTION

The present invention relates to the synthesis of ethanol from biomass and, more particularly to such synthesis by a catalytic thermochemical process.

Conversion of biomass to ethanol by fermentation techniques is a well practiced process, especially with the emerging importance of gasohol in today's economy. Conventional fermentation techniques, however, suffer from a number of drawbacks including, for example, protracted reaction times, the need for sterile reaction conditions, the need for purified feedstocks, the production of voluminous by-products, and an energy intensive distillation operation for recovery of ethanol from water. The need for an alternate route for converting biomass to ethanol thus exists. Unfortunately, no alternative process has emerged in the marketplace.

In studying the reaction mechanisms involved in fermentation of sugar, it has been reported that an aqueous solution of some sugars can be converted to lactic acid in the presence of an alkali metal or alkaline earth metal hydroxide or oxide. Montgomery and Ronca, "Chemical Production" of Lactic and Other Acids from Molasses", *Industrial and Engineering Chemistry,* Vol. 45, No. 5, pp 1136–1147 (1953) and references cited therein. In other unrelated research, it has been reported that certain alkali metal or alkaline earth metal lactate salts could be decarboxylated to produce a mixture of several organic liquids and gases and on occasion some ethanol. Hanriot, "Sur la decomposition pyrogenee des acides de la serie grasse", Nouv. Ser. T. XLV, Societe Chimique, pp 79–81 (1886); Buchner and Meisenheimer, "Die chemischen Vorgänge bei der alkoholischen Gährung" *Berk. deut. chem. Ges.,* 38, 620–630 (1905) and Fischer, Schrader and Wolter, "Über die Entkarboxylierung der Milschäure, *Gesamm. Abh. Kenntnis Kohle,* 6, 99–107 (1923). For further studies on lactic acid as it may relate to fermentation of sugars, reference is made to the text by C. H. Holten, *Lactic Acid: Properties in Chemistry of Lactic Acid and Derivatives,* Verlag Chemie, GmbH, Copenhagen, Denmark.

The present invention has solved the long standing problem of converting biomass into ethanol by a process which does not involve fermentation. Also, substantially all of the disadvantages inherent in conventional fermentation of biomass are obviated by the present invention.

BROAD STATEMENT OF THE INVENTION

The present invention is a method for thermochemically converting a carbohydrate material into ethanol. Such method comprises establishing an aqueous reaction mixture of the carbohydrate and a metal salt in a reaction zone held at elevated temperature to form an intermediate metallic complex (eg. metallic sucrate) and/or a metallic lactate salt. The metallic salt then is separated from the reaction mixture and pyrolyzed in a pyrolysis zone in the presence of water to form said ethanol. Suitable carbohydrate materials are sacchariferous materials such as monosaccharides, polysaaccharides, and oligosaccharides. Another aspect of the present invention involves the thermochemical conversion of the carbohydrate material into ethanol wherein the carbohydrate material, the metal salt, and water are established in a reaction zone for the one-step conversion of the carbohydrate material into ethanol. In this aspect of the invention the metal of the metallic salt is restricted to a metal which when formed into the by-product metallic carbonate, such carbonate will be decomposed in situ to generate a metallic oxide or hydroxide. A further aspect of the present invention is a method for making a liquid combustible fuel blend of combustible (fossil) fuel (eg. fuel oil, diesel fuel, kerosene, gasoline, etc.) and ethanol, though preferably a gasoline-alcohol blend (gasohol), wherein the ethanol is made by the thermochemical conversion of a carbohydrate material as described above and the product ethanol is blended with the combustible fuel, eg. gasoline.

Advantages of the present invention include quick reaction times for converting carbohydrate feed into ethanol and specifically the ability to reduce the reaction time for making ethanol from 16–24 hours by conventional fermentation to a matter of minutes by the thermochemical process of the present invention. Another advantage of the present invention is the ability to efficiently and effectively operate with impure carbohydrate feeds which cannot be tolerated by conventional fermentation techniques. A further advantage is the ability to convert many carbohydrate materials into ethanol which are unsuitable as feedstock for conventional fermentation production of ethanol. A still further advantage of the present invention is the probable volumetric reduction of by-products from the present invention, especially compared to by-products, such as stillage, from conventional fermentation techniques. Yet another advantage is the minimization of energy consumption required for purification of the ethanol product. These and other advantages will become readily apparent to those skilled in the art based on the disclosure herein contained.

DETAILED DESCRIPTION OF THE INVENTION

The process of thermochemically converting carbohydrate material feedstock into ethanol involves multiple chemical reaction steps which means flexibility in designing different operational modes for practicing the present invention. Though dominant chemical reactions can be attributed to the production of ethanol from carbohydrate feedstock, it should be recognized that completing reactions do occur during the process which often lead to by-products and lower yields of ethanol. In order to more fully appreciate the chemistry involved in the thermochemical process of the present invention, the following postulated reactions for the process are given. It should be understood that such reactions are given for purposes of illustration only and are not to be interpreted as a limitation on the present invention. Such chemical reaction steps in the present process are as follows:

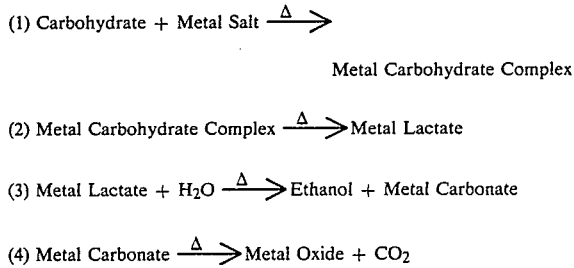

(1) Carbohydrate + Metal Salt $\xrightarrow{\Delta}$ Metal Carbohydrate Complex (2) Metal Carbohydrate Complex $\xrightarrow{\Delta}$ Metal Lactate (3) Metal Lactate + $H_2O$ $\xrightarrow{\Delta}$ Ethanol + Metal Carbonate (4) Metal Carbonate $\xrightarrow{\Delta}$ Metal Oxide + $CO_2$ Several observations can be made based upon the foregoing reaction steps. Initially, it can be seen that a metal carbonate salt results during the ethanol production step and that such carbonate salt can be conventional techniques to metal oxide (or hydroxide) plus carbon dioxide. In practical terms this means that while a wide variety of metal salts can be used in the process, clearly oxide salts may be preferred in order to take advantage of the renewable source of oxide resulting in the process. Such renewable source of the metal salt may be understood further by reference to a specific embodiment of the present invention wherein sucrose is converted into ethanol utilizing calcium oxide catalyst. With such reactants for the process, the chemical reaction steps involved are as follows:

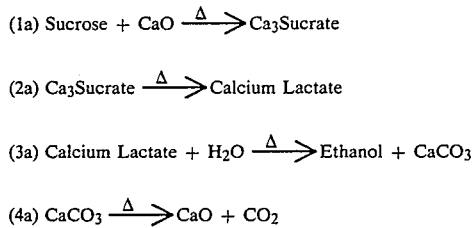

(1a) Sucrose + CaO $\xrightarrow{\Delta}$ $Ca_3$Sucrate (2a) $Ca_3$Sucrate $\xrightarrow{\Delta}$ Calcium Lactate (3a) Calcium Lactate + $H_2O$ $\xrightarrow{\Delta}$ Ethanol + $CaCO_3$ (4a) $CaCO_3$ $\xrightarrow{\Delta}$ CaO + $CO_2$ It should be clearly understood that the foregoing chemical synthesis utilizing sucrose and calcium oxide feed materials is for purposes of illustrating the present invention and is in no way a limitation on the present invention. From such chemical reaction steps, it can be seen that the calcium oxide catalyst is a renewable product from the process which clearly provides certain economies to practice of the present invention. The term "catalyst" to describe the metallic salt herein is used in the sense that there is no net consumption of the metallic salt in the process as the metallic salt is regenerable to its oxide or hydroxide form.

Based upon the foregoing reaction mechanisms postulated for the present invention, it can be seen that the present process possibly can be operated in step-wise fashion (assuming the ability to isolate the various products of the individual reaction steps). One of the clear advantages of the present invention is the discovery that by judicious selection of the reaction conditions prevailing in the process (for example, temperature, pressure, time, and the like), the present process indeed can be operated in a distinct step-wise method following the chemical reactions outlined above. Moreover, the present process has the flexibility to be operated in various combinations of the reaction steps given above for additional flexibility in operating the process efficiently and economically based upon availability of equipment, various carbohydrate feedstocks, various metal salts, and the like. Thus, the present process can be optimized for various combinations of reactants and reaction conditions available to any operator of the process. Conventional fermentation techniques for conversion of sugar to ethanol clearly do not have the choice of the various operational modes available to the present invention.

The individual chemical reaction steps involved in the process can be combined in several ways for the production of ethanol. Various of these combinations provide distinct advantages over other combinations as will be readily apparent to those skilled in this art. For example, the four chemical reaction steps can be operated individually, the first and second steps can be operated together, the first three steps can be operated together and the like. In fact by selection of the appropriate metal for use in the process, the fourth step will occur in situ under the reaction conditions prevailing in the process. An advantage of isolating the metal carbohydrate complex from step (1) would be to reduce the volume of water typically present in this step which would make ultimate separation of product ethanol from water a less energy intensive operation. The same advantage can be realized also by operating the first two steps together for recovery of the metal lactate. Various other combinations clearly can be conceived by those skilled in the art based upon the disclosure herein contained. It is of note, though, that maximization of yields from the individual steps and/or purification may be achieved by a step-wise practice of the process rather than a one-step direct conversion of carbohydrate feedstock to ethanol.

Suitable carbohydrate feedstock material for the present invention most often will be saccharides and often the term sugar will be used for their description. Simple monosaccharides for use in the present process include hexoses such as, for example, glucose, mannose, gallactose, gulose, formose, and fructose; pentoses such as, for example, arabinose, xylose, ribose, and rhamnose; tetroses such as, for example, erythrose and threose; and trioses such as, example, glycerose. Derivatives of saccharides such as, for example, gluconic acid, mono-, and diphosphatates of fructose, etc., also can be used in the process. It should be noted that conversion of pentose sugars (for example hemicellulose from wood hydrolysis) by the present process will result in the production of one mole of a lactate salt and probably one mole of a glycolate salt from reaction step (2). The thermochemical decomposition of such salts would yield one equivalent of ethanol and one equivalent of methanol which mixture would be suitable as a fuel ingredient. The important consideration in the use of pentose sugars is that they will not poison the reaction which occurs with conventional fermentation processes because of the effect of by-product furfuraldehyde.

Additional carbohydrate feedstock include disaccharides such as, for example, sucrose, maltose, and the like. Other suitable feedstock include polysaccharoses and oligosaccharides. Such sugars can be derived from sugar crops such as sugar cane, sugar beets, or sweet sorghum; or by the partial or complete hydrolysis of starch or starch-like materials in grains such as corn, wheat, oats, and the like; or can be derived from other crops such as potatoes, yams, manioc, and the like.

Additional sugars suitable as feedstock for the present invention can be derived from lignocellulosic materials such as agricultural and forestry residues or by-products such as, for example, corn stalks or corn cobs, sawdust and other forest residues, bagasse, cattle or other manure, leaves, newspaper from municipal waste, and the like. Such agricultural and forestry residues preferably are hydrolyzed or at least partially hydrolylzed to sugars or oligosaccharides prior to their admission to the present process. The present process also may utilize soluble polysaccharides such as, for example, soluble starch or polysaccharides that have been pretreated to reduce the degree of crystallinity (e.g. amorphous cellulose).

Thus, it can be seen that a myriad of materials can be used directly or converted into suitable feedstock for use in the present process. Such materials need not be rigorously purified for admission into the process as is required in conventional fermentation processes, because typical fermentation poisonous materials do not interfere with the thermochemical process of the present invention.

Suitable catalysts for use in the present invention are those metal salts that can display a basic reaction in an acidic environment. Preferable catalysts are oxides, hydroxides, and carbonates of alkali metals and alkaline earth metals. For present purposes, alkali metals include lithium, sodium, potassium, rubidium, and cesium; and alkaline earth metals include beryllium, magnesium, calcium, strontium, and barium. Additional catalysts useful in the present invention include salts of amphoteric or transition metals such as salts of, for example, aluminum, zinc, lead, barium, cadmium, magnesium, mercury, silver, cobalt, manganese, bismuth, gallium, niobium, copper, iron, nickel, and the like, preferably provided as an oxide, hydroxide, or carbonate. Further suitable metallic salts include complex metallic salts which contain one metal plus either a second metal or non-metal or other anion. Representative anions of such complex metallic salts, for example, can be selected from the following: arsenate, chromate, ferricyanide, carbonate, silicate, molybdate, (dibasic, tri-basic, pyro, meta, ortho) phosphate, plumbite, sulfate, aluminate, bisulfite, (meta or tetra) borate, chlorate, chloraurate, chloroplatinate, dithionate, manganate, nitrite, selenate (meta or ortho) silicate, stannate, sulfite, tartrate, thiocyanate, thiosulfate, tungstate, vanadate, and the like. Even more complex metallic salts such as salts of heteropolyacids (eg. sodium salt or phosphomolybdic acid) may be useful in the process also. It should be recognized that combinations of such salts can be used as well as materials which generate the suitable salt in the reaction mixture in situ.

As previously noted based upon the chemical reaction steps involved in the process, metal oxides may be preferred for use in the process since metal oxides can be generated from the process for recycle thereto. Moreover, for continuous operation of the present invention selection of a metal whose carbonate decomposes to metal oxide and carbon dioxide gas under the reaction conditions prevailing in the process may be desired for self-generating catalysts for the process. Such metal carbonates include, for example, magnesium carbonate, zinc carbonate, copper carbonate (possibly complexed with $Cu(OH)_2$), cadmium carbonate, mercurous carbonate, silver (I) carbonate, cobalt (II) carbonate, iron (II) carbonate, manganese carbonate, nickel carbonate, and lead carbonate, which can be decomposed at the pyrolysis temperatures of the process.

Since water is involved in the pyrolysis of the metallic lactate to ethanol and metal carbonate salt, water is the preferred solvent of choice for use in the present process. It should be recognized, however, that excessive quantities of water in the reaction mixture may not be desirable because of later separation problems of product ethanol from water-ethanol mixtures. It, then, may be desirable to employ suitable organic solvents in the process to aid in subsequent purification efforts for recovery of the desired ethanol product. Such organic solvents preferably are water soluble though this is not necessary. A particularly preferred organic solvent for use with water as a solvent system in the present invention is ethanol since ethanol is the product being made. While a solvent is not strictly required for production of the metal lactate from the carbohydrate feedstock, many carbohydrate feedstock materials for use in the present process will be in aqueous form and thus more often the entire process will be conducted in an aqueous solvent. It should be recognized, however, that in the chemical pyrolysis of the metal lactate to ethanol that the water required for the process may be in the vapor phase.

Reaction conditions for the present process include temperatures ranging from between about 150° to about 400° C. and above. The actual temperatures employed in the process will depend necessarily upon which reaction steps are being run concurrently and upon the particular feedstock and metal salt employed in the process. Preferred reaction temperatures for the overall process range from about 275° to 400° C. Since such elevated temperatures are required for the process, pressures preferably will be in the superatmospheric range especially when it is desired to retain the aqueous solvents in the process in the liquid phase. It should be recognized that atmospheric pressure and pressures slightly above atmospheric may find use in the present process. Preferably pressures range from about 500 to about 3,000 psig, though it may be convenient in running the process to maintain autogenous pressure. Again, the pressure used in the process will depend necessarily upon the other reaction conditions and reactants used in the process.

The process additionally may be conducted under an inert gas blanket or inert atmosphere especially when the process is conducted in several distinct stages. Such inert gas atmosphere minimizes side reactions in the process. Suitable inert or non-reactive gases in the process include, for example, nitrogen, carbon dioxide, propane, argon, and the like and even mixtures thereof.

The primary product of the present invention is ethanol though a variety of other products and by-products normally will result from the process. One such product is a metal carbonate which suitably is converted to additional metal oxide for use in the process. Other products that may be produced by the process include, for example, methanol and 2,4-dihydroxy-3-pentanone. It will be appreciated that the particular by-products resulting from the process will necessarily depend upon particular reactants used in the process and especially the carbohydrate feedstock of choice, upon the particular reaction conditions maintained in the process, whether the process is run in distinct steps or as a one-step direct conversion ethanol process, and the like. Such additional organic products produced by the process may be separated from the ethanol by fractionation techniques including (molecular) distillation and crystallization, or can be left with the product ethanol for use as a fuel additive or as a chemical feedstock for additional processing.

In practicing the present process, it should be recognized that yields of the products resulting from the various reaction steps necessarily also depend upon the concentration of the reactants used as well as the other reaction conditions (e.g. time, temperature, pressure, etc.). In the formation of the metal lactate, prior work has shown that yields thereof depend upon the concentration of both the carbohydrate feedstock and the metal salt catalyst, as would be expected. Since the other reaction conditions established in the process (e.g. time, temperature, and pressure) appear to control the yields of products and by-products in the present process to a greater extent than the particular ratio of reactants used, the proportion of reactants used in the process will be adjusted accordingly. It is important to note, however, that sufficient water must be present during the pyrolysis of the metal lactate salt intermediate in order to achieve the required ethanol and metal carbonate products. Such proportion of water, though, should not be excessive as subsequent purification efforts of the ethanol would be retarded thereby.

In connection with the various operational modes which can be designed for the process based on the series of reaction steps given above, it will be appreciated that a variety of equipment can be interconnected for reducing such operational modes to commercial practice. In order to further illustrate several presently preferred operational modes and typical equipment suitable for implementation of such modes, the following process systems discussion is given. For a one-step process for directly converting carbohydrate feedstock into product ethanol, the carbohydrate feedstock suitably in an aqueous solvent can be fed along with the metallic salt, preferably as an aqueous slurry or solution, to an agitated reaction vessel having freeboard space above the liquid level maintained therein. With the reaction vessel maintained at operating conditions, an ethanol product stream containing ethanol, carbon dioxide, water, and other volatile material can be vented from the freeboard space within the reactor continuously while the carbohydrate feedstock is fed to the reaction vessel continuously. Metal carbonate product formed from the reaction can be removed as an underflow from the reaction vessel and sent to a combustion zone using coal, biomass, or other convenient fuel to regenerate metal oxide and carbon dioxide gas therefrom. The metal oxide then can be recycled to the reaction vessel on a continuous basis, if required. Alternatively, for those metal carbonates which will decompose under the reaction conditions (for example, zinc carbonate at about 300° C., copper carbonate at about 200° C., and the like), the metal oxide will be regenerated in situ in the reactor so that at most only make-up metal salts should be required to be passed into the reaction zone. Separation of the ethanol from the ethanol product stream is practiced as described above.

Alternatively, for insoluble or slightly soluble metal salts, a fixed bed of the catalyst metal salt can be maintained within a flow reaction vessel of suitable design (e.g., a tubular flow reactor) and an aqueous solution or dispersion of the carbohydrate material passed therethrough with the aqueous ethanol product stream withdrawn therefrom.

For a two-step process wherein either a metallic carbohydrate complex of the metal salt (eg. a metallic sucrate) or metallic lactate salt is recovered and thence converted into product ethanol, the carbohydrate feedstock and metallic salt can be fed to a reaction vessel such as described for the one-step process. Following the production of the metallic sucrate salt or metallic lactate salt, the reaction mixture can be conventionally cooled for precipitation of the salt therefrom. Other methods for separation of the solid salt from the reaction mixture include evaporation or distillation of the aqueous phase therefrom. Other conventional separation techniques additionally may be employed. Separation of the precipitated salt from the aqueous reaction mixture effectively reduces the amount of water carried forward in the process for reducing the load placed on the ethanol purification step of the process. Even with separation of the salt by distillation of the aqueous phase from the reaction mixture, a less energy intensive process results because this distillation separation step requires no reflux nor is it an azeotropic distillation, which techniques are required in conventional fermentation production of ethanol for its separation and recovery from water. With production of a metal lactate salt by the two-step process, such recovered salt can be pyrolyzed to product ethanol as described above. With separation and recovery of a metallic sucrate salt, such salt can be converted to product ethanol in a one-step process or can be converted to the metallic lactate salt which can be recovered and the recovered lactate salt pyrolyzed to product ethanol. Possible optimization of yields of the various intermediates may be realized by such distinct step-wise practice of the process as well as a reduction of the proportion of water carried forward in the process.

The recovery of the intermediate metallic carbohydrate complex (eg. metallic sucrate salt) and metallic lactate salt separately may be termed a multi-step process for production of ethanol according to the present invention. The metallic lactate salt, whether produced directly from the carbohydrate feedstock or produced from the recovered metallic sucrate salt intermediate, can be pyrolyzed to ethanol utilizing a variety of equipment. For example, a fluidized bed of the concentrated metallic lactate salt, optionally containing inert solids or other reactant solids (eg. metal salt catalyst), can be established utilizing a supporting gas of carbon dioxide or the like preferably containing steam for providing the water necessary for the pyrolysis reaction to occur as desired. The ethanol product stream would be vented from the reactor and sent to purification operations. Solids withdrawn from the fluidized bed can include the metal carbonate product or metal oxide, depending upon the particular metal utilized in the process and the particular pyrolysis conditions established in the fluidized bed reactor. Alternatively, a falling-bed type reactor also could be employed as well as could any other convenient gas-solids reactor.

In order to more fully appreciate the process of the present invention, the following illustrative design example for converting sugar to ethanol utilizing a lime catalyst by the two-step process of the present invention wherein the calcium lactate intermediate is recovered, is given. An aqueous sugar (sucrose) solution is fed to a tubular flow reactor maintained at about 250° C. along with a flow of recycled lime (calcium oxide) and optionally recycled water. The residence time of the reactants in the tubular flow reactor is about 2 minutes. The aqueous reaction mixture withdrawn from the tubular flow reactor is sent to a flash evaporator and precipitator wherein water is flash-evaporated from the reaction mixture and the calcium lactate is precipitated therefrom. The water may be recycled directly to the tubular flow reactor or can be used to form additional aqueous sugar feedstock for the process. The concentrated calcium lactate is sent to a fluidized pyrolysis bed maintained at about 250° C. for about 1 minute residence time. Solids in the fluidized pyrolysis bed are maintained in random motion utilizing carbon dioxide gas recycled from a later step of the process. Ethanol, carbon dioxide, water and other volatile by-products are vented from the fluidized pyrolysis bed and sent to purification operations for recovery of product ethanol. Limestone (calcium carbonate) withdrawn from the fluidized pyrolysis bed is sent to a lime kiln, optionally along with a flow of miscellaneous chemicals recovered from the ethanol purification operations. Additionally, bagasse or other convenient fuel can be combusted in the kiln for converting the limestone into lime (calcium oxide) and carbon dioxide gas which is used to fluidize the solids in the fluidized pyrolysis bed. The regenerated lime then can be sent back to the tubular flow reactor as indicated above. Again, it will be appreciated that this conceptual process mode is given for purposes of illustration and not by way of limitation of the present invention.

Materials of construction for the various zones are conventional for this type of high temperature, high pressure operation. Thus, where corrosion-resistant materials are required, use of austenitic stainless steel, plastic, glass-lined steel, wood, or even clay may be used. Concrete or steel can be used where corrosion or erosion is inconsequential. Piping, ductwork, and other appurtenant lines will be of similar material, conventionally constructed. It will be appreciated that various of the tanks, lines, reactors, and the like can be multiple, series, cascade, or parallel connected for additional treating time or capacity, or for special effects.

The following examples show how the present invention can be practiced but should not be construed as limiting. In this application, all proportions, percentages, and ratios are by weight, and all units are in the metric system unless otherwise expressly indicated.

EXAMPLE 1

Conversion of Sucrose to Ethanol

A one gallon, stainless steel, Autoclave Engineers' magna drivve autoclave was set up with both vapor phase and liquid sampling tubes. The liquid phase dip tube was arranged so the line could be back-flushed with nitrogen. In the glass liner of the autoclave was placed 137 grams of sucrose (table sugar), 118.6 grams of calcium hydroxide and 580 ml of deionized water. An additional 100 ml of deionized water was placed between the liner and the autoclave. The autoclave was purged twice with nitrogen and the pressure was returned to atmospheric. The autoclave was heated, with stirring, for two hours to 300° C. An 18.0 gram sample of tan liquid was then removed. This is referred to as the zero time sample. The reactor temperature was maintained at 300°±3°. Additional samples were taken at the following times (after zero time sample): 30 mins (13.7 gm), 1 hr (15.1 gm), 2 hr (15.1 gm), 3.5 hrs (17.8 g), 5 hrs (17.6 gm). A vapor sample (12.9 gm of condensed liquid) was also removed at 5 hours. The heater and stirrer were shut off and the autoclave was allowed to cool down overnight. The residual slurry in the glass liner was 516 grams and an additional 157 grams of material was recovered from between the autoclave and glass liner. Also 15 grams of material was recovered by flushing the lines. The total material recovered was 798 grams compared to 935.6 grams charged.

Some of the samples were analyzed for ethanol by gas chromatography. One ml of each of the samples was diluted up to 10 ml with deionized water in a 10 ml volumetric flask. The G.C. analyses were carried out on a Varian model 1400 GC with a 10 percent Carbowax 20M glass column 10 feet long. The column was heated to 80° C. The ethanol was identified by comparing retention time with an ethanol standard. The concentration of the ethanol was calculated using a standard curve based on 1000 ppm, 500 ppm, and 100 ppm levels of ethanol standards. The following results were obtained:

| Sample Time (hr) | Sample Weight (gm) | Ethanol as Weight Percent of Volatile Organics | Ethanol (ppm) |
| --- | --- | --- | --- |
| 0 - liquid | 18.00 | 66 | 1700 |
| 2 - liquid | 15.1 | 57 | 2500 |
| 5 - liquid | 690.6 | 50 | 2700 |
| 5 - vapor | 12.9 | — | 16000 |

The above-tabulated results clearly show that ethanol can be made directly from sucrose by a one-step reaction process. Thus, the chemistry of the reaction is established.

EXAMPLE 2

Conversion of Sucrose to Ethanol

To a one liter, stainless steel, autoclave (like that autoclave described in Example 1) was charged 111 gms of sucrose (table sugar), 73 gms of calcium oxide, and 405 ml of deionized water. The autoclave was pressure tested with nitrogen at 2,000 psig and the pressure returned to atmospheric. The autoclave was heated, with stirring, for 1.5 hours to a temperature of 300° C. The reactor temperature then was maintained at 300°±1° C. for an additional one hour. The heater and stirrer where shut off and the autoclave allowed to cool down overnight. The residual liquid slurry in the autoclave weighed 581 gms compared to the 589 gms of material that was originally charged to the autoclave.

The residual slurry was filtered by gravity to remove solids and the liquid filtrate analyzed for ethanol by the gas chromatography procedure described in Example 1. The liquid sample was found to contain 9,100 micrograms of ethanol per milliliter of liquid. Also, 67% by weight of the volatile reaction product mixture evolved during the course of the reaction was determined to be ethanol. Again, the chemistry of the reaction is established in this example.

EXAMPLE 3

Conversion of Sucrose to Ethanol

To the one liter autoclave described in Example 2 was charged 74 gms of sucrose, 70 gms of sodium hydroxide pellets, and 500 ml of deionized water. Oxygen then was introduced into the head space in the autoclave to a pressure of 400 psig. The reactor was heated to 267° C. over a three hour time period. At this temperature the autoclave pressure was determined to be 1,000 psig. The autoclave was maintained at 267°±5° C. with stirring for an additional 95 minutes during which time the pressure in the autoclave dropped to about 725 psig.

A total of 626 gms of liquid slurry was recovered from the reaction mixture which represents over 97% of the 644 gms of material initially charged to the reactor. The slurry was filtered and the filtrate analyzed for ethanol by the gas chromatography technique described in connection with Example 1. The filtrate was determined to contain 7.0 gms of ethanol. Also, ethanol represents 94.7% by weight of the volatile organic materials in the reaction product. Again, the chemistry of the reaction is demonstrated in this example.

EXAMPLE 4

Conversion of Sucrose to Ethanol

To the one liter autoclave described in Example 2 was charged 111 gms of sucrose, 106 gms of zinc oxide, and 405 ml of deionized water. The autoclave was sealed and pressure checked at 2,000 psig with nitrogen gas. After releasing the pressure to atmospheric, the reactor was heated to 300° C. over a 70 minute time period, and then maintained at 300°±2° C. for 6 hours. After the autoclave had cooled to room temperature overnight, there was a residual pressure in the autoclave of 400 psig. This pressure is due to carbon dioxide gas being released by the decomposition of zinc carbonate under the reaction conditions. Note that in Examples 1 and 2 the pressure in the reactor upon its cooling was not above atmospheric pressure which is consistent with the formation of calcium carbonate in the reaction which is not decomposable under the reaction conditions. Also, there was no increase in the autoclave pressure in Example 3 following termination of the reaction which again is consistent with the formation of by-product sodium carbonate which is not decomposable under the reaction conditions.

A total of 584 gms of liquid slurry was recovered from the autoclave. The filtrate was analyzed by the gas chromatography procedure described above and found to contain 830 micrograms per milliliter of ethanol. Accordingly, this example demonstrates the one-step direct conversion of biomass to ethanol utilizing a metal salt whose carbonate is decomposable under the reaction conditions established in the reactor. This means that the reactor need only be charged with additional carbohydrate feedstock (and perhaps water) continuously for producing ethanol since the metal salt is continuously regenerated in the process.

EXAMPLE 5

Conversion of Starch to Ethanol

The one liter autoclave described above was charged with 115 gms of soluble starch, 93 gms of cuprous oxide, and 405 ml of water. The autoclave was pressure tested and then heated to the reaction temperature used in Example 4. After the autoclave was cooled to room temperature overnight, there was a residual pressure of 275 psig therein due to carbon dioxide gas in the autoclave. This carbon dioxide gas is produced by the decomposition of cuprous carbonate which is formed in the reaction to regenerate the cuprous oxide catalyst. The liquid slurry was recovered from the autoclave and determined to weigh 568 gms. Gas chromatography analysis revealed that the liquid slurry contained 180 micrograms per milliliter of ethanol. The results of this example show that a complex carbohydrate feedstock (starch) can be successfully directly converted to ethanol according to the precepts of the present invention. The results of this example further demonstrate that cuprous oxide used in the process can be continuously regenerated from its corresponding by-product carbonate formed in the process.

We claim:

1. A method for making a liquid fuel-ethanol blend which comprises:
    establishing an aqueous reaction mixture of a carbohydrate material, a metal salt, and water in a reaction zone held at elevated temperature of about 150°–300° C. to form an intermediate carbohydrate complex of said metal and/or a metal lactate salt;
    pyrolyzing at a temperature of about 275°–400° C. said complex and/or lactate salt in the presence of water in a pyrolysis zone to form ethanol;
    recovering said ethanol; and
    blending combustible liquid fuel with said ethanol.

2. The method of claim 1 wherein said liquid fuel is a fossil fuel selected from diesel fuel, fuel oil, kerosene, and gasoline.

3. The method of claim 1 wherein said carbohydrate material is a sacchariferous material.

4. The method of claim 3 wherein said sacchariferous material is a monosaccharide, a polysaccharide, or an oligosaccharide.

5. The method of claim 4 wherein said sacchariferous material is selected from glucose, sucrose, arabinose, gallactose, formose, fructose, mannose, rhamnose, mono- and diphosphates of fructose, maltose, gluconic acid, gulose, xylose and ribose.

6. The method of claim 4 wherein said sacchariferous material is derived from sugar cane, sugar beets, sweet sorghum, grains, potatoes, yams, or manioc.

7. The method of claim 3 wherein said sacchariferous material is a hydrolysis product of lignocellulosic material.

8. The method of claim 1 wherein said metal salt is a metal hydroxide, oxide, or carbonate.

9. The method of claim 1 or 8 wherein said metal of said metal salt is an 25 alkali metal or alkaline earth metal.

10. The method of claim 9 wherein said metal of said metal salt is calcium, sodium, or magnesium.

11. The method of claim 1 or 8 wherein said metal of said salt is selected from aluminum, zinc, lead, barium, cadmium, magnesium, mercury, silver, cobalt, manganese, copper, iron, and nickel.

12. The method of claim 11 wherein said metal of said metal salt is selected from magnesium, zinc, copper, lead, cadmium, mercury, silver, cobalt, iron, manganese, and nickel.

13. The method of claim 1 wherein the pressure for said complex and/or lactate metal salt formation is at least atmospheric.

14. The method of claim 1 wherein the pressure for said pyrolysis is at least atmospheric.

15. The method of claim 1 wherein said complex and/or lactate metal salt formation and said pyrolysis are conducted, independently, at a pressure of between about 500 and 3000 psig.

16. The method of claim 1 wherein an organic cosolvent is used in said reaction mixture established in said reaction zone and in said pyrolysis zone.

17. The method of claim 16 wherein said cosolvent is ethanol.

18. The method of claim 1 wherein said reaction mixture of said carbohydrate material and said metal salt is held under conditions adequate for said intermediate carbohydrate complex of said metal to be formed, the volume of water in said aqueous complex aqueous complex mixture is reduced, and then said complex is heated for forming said lactate metal salt.

19. The method of claim 1 wherein by-product metallic carbonate formed with said ethanol is recovered, converted to metal oxide and carbon dioxide, and said metal oxide is recycled to said reaction mixture.

20. The method of claim 1 wherein said reaction zone and said pyrolysis zone are the same zone.

21. The method of claim 1 wherein said complex is formed in said reaction zone.

22. The method of claim 1 wherein said metal lactate salt is formed in said reaction zone.

23. The method of claim 12 wherein said reaction zone and said pyrolysis zone are the same zones, and said metallic carbonate formed therein is converted to carbon dioxide and metal oxide or hydroxide in situ.

24. The method of claim 1 wherein said complex and/or lactate salt formed in said pyrolysis zone is separated from said reaction mixture, said separate complex and/or lactate salt admitted into said pyrolysis zone to form said ethanol, said metallic carbonate formed in said pyrolysis zone being converted in situ to a metal oxide or hydroxide and carbon dioxide, and said metal oxide or hydroxide is recycled to said reaction zone.

* * * * *